United States Patent [19]
Freitas et al.

[11] Patent Number: 5,486,185
[45] Date of Patent: Jan. 23, 1996

[54] SURGICAL APPARATUS

[75] Inventors: Michael W. Freitas, Irving; Wayne D. Miller, Bedford, both of Tex.

[73] Assignee: Dexide, Inc., Fort Worth, Tex.

[21] Appl. No.: 723,190

[22] Filed: Jun. 28, 1991

Related U.S. Application Data

[63] Continuation of Ser. No. 629,993, Dec. 19, 1990, abandoned, which is a continuation of Ser. No. 303,850, Jan. 30, 1989, abandoned.

[51] Int. Cl.⁶ .......................... A61B 17/12; A61B 17/28; A61B 17/32
[52] U.S. Cl. .......................... 606/142; 606/174; 606/206
[58] Field of Search .......................... 606/142, 170, 606/171, 174, 205, 206, 119, 140, 141, 207; 604/167, 169

[56] References Cited

U.S. PATENT DOCUMENTS

| 1,294,284 | 2/1919 | Logeman. | |
|---|---|---|---|
| 2,968,041 | 9/1958 | Skold | 1/49.1 |
| 3,232,089 | 5/1961 | Samuels et al. | 72/410 |
| 3,713,533 | 1/1973 | Reimels | 206/56 |
| 3,777,538 | 12/1973 | Weatherly et al. | 72/410 |
| 3,820,544 | 6/1974 | Semm | 606/141 X |
| 4,027,510 | 6/1977 | Hiltebrandt | 72/37 |
| 4,152,920 | 5/1979 | Green | 72/410 |
| 4,299,224 | 11/1981 | Noiles | 128/325 |
| 4,440,170 | 4/1984 | Golden et al. | 128/325 |
| 4,646,751 | 3/1987 | Maslanka | 128/751 |
| 4,674,501 | 6/1987 | Greenberg | 606/174 |
| 4,696,298 | 9/1987 | Higgins et al. | 128/305 |
| 4,706,668 | 11/1987 | Backer | 606/142 |
| 4,759,364 | 7/1988 | Boebel | 606/142 |

Primary Examiner—Michael H. Thaler
Attorney, Agent, or Firm—Robert A. Felsman; Mark D. Perdue

[57] ABSTRACT

A surgical apparatus for use in laparoscopic surgery being adaptable to provide for clipping, cutting or clamping. The device has a probe having an instrument attached to one end to be inserted in a patient. Slidably disposed over the probe is a sliding sleeve which applies force to the instrument end of the probe to effect the desired action. In one embodiment the probe may be rotatable, while in another embodiment the instrument ends are interchangeable.

8 Claims, 3 Drawing Sheets

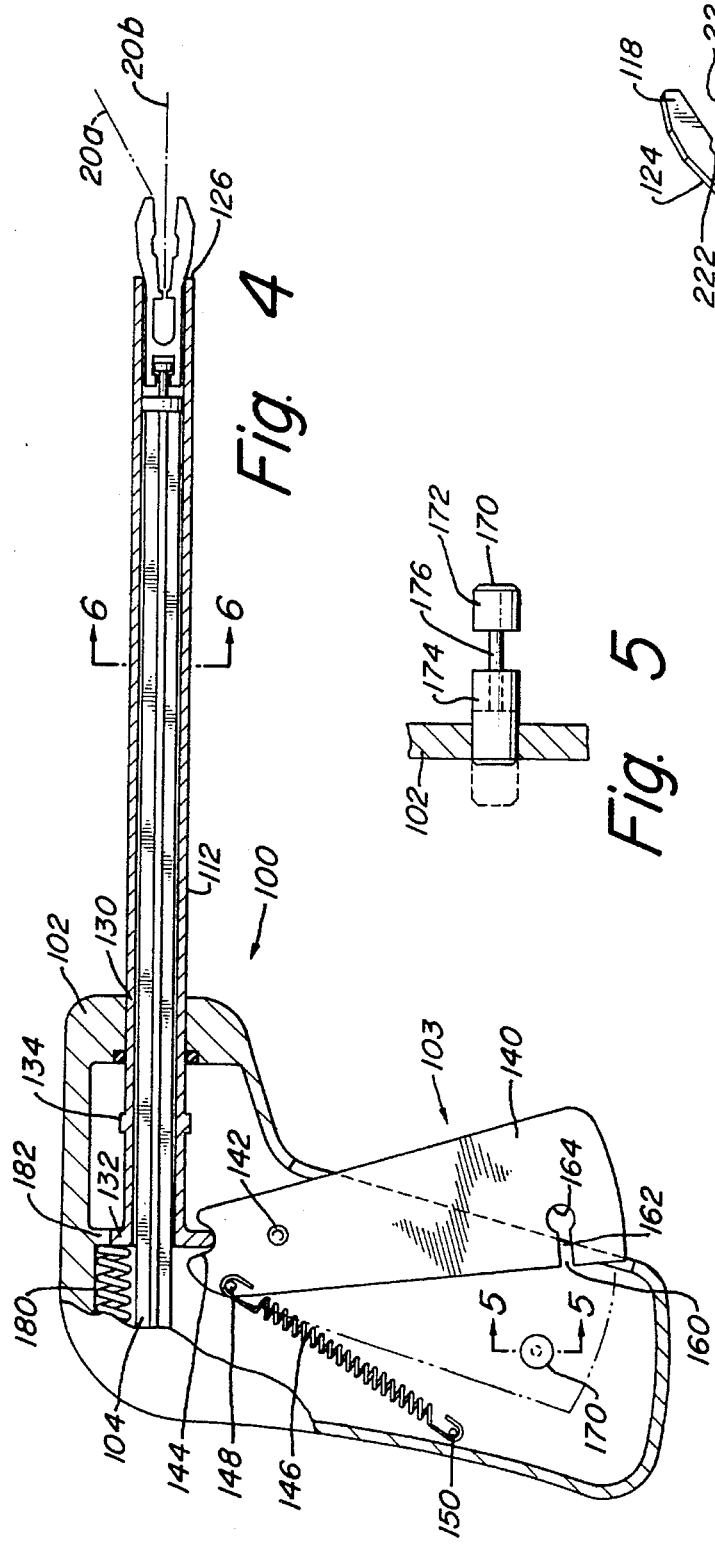

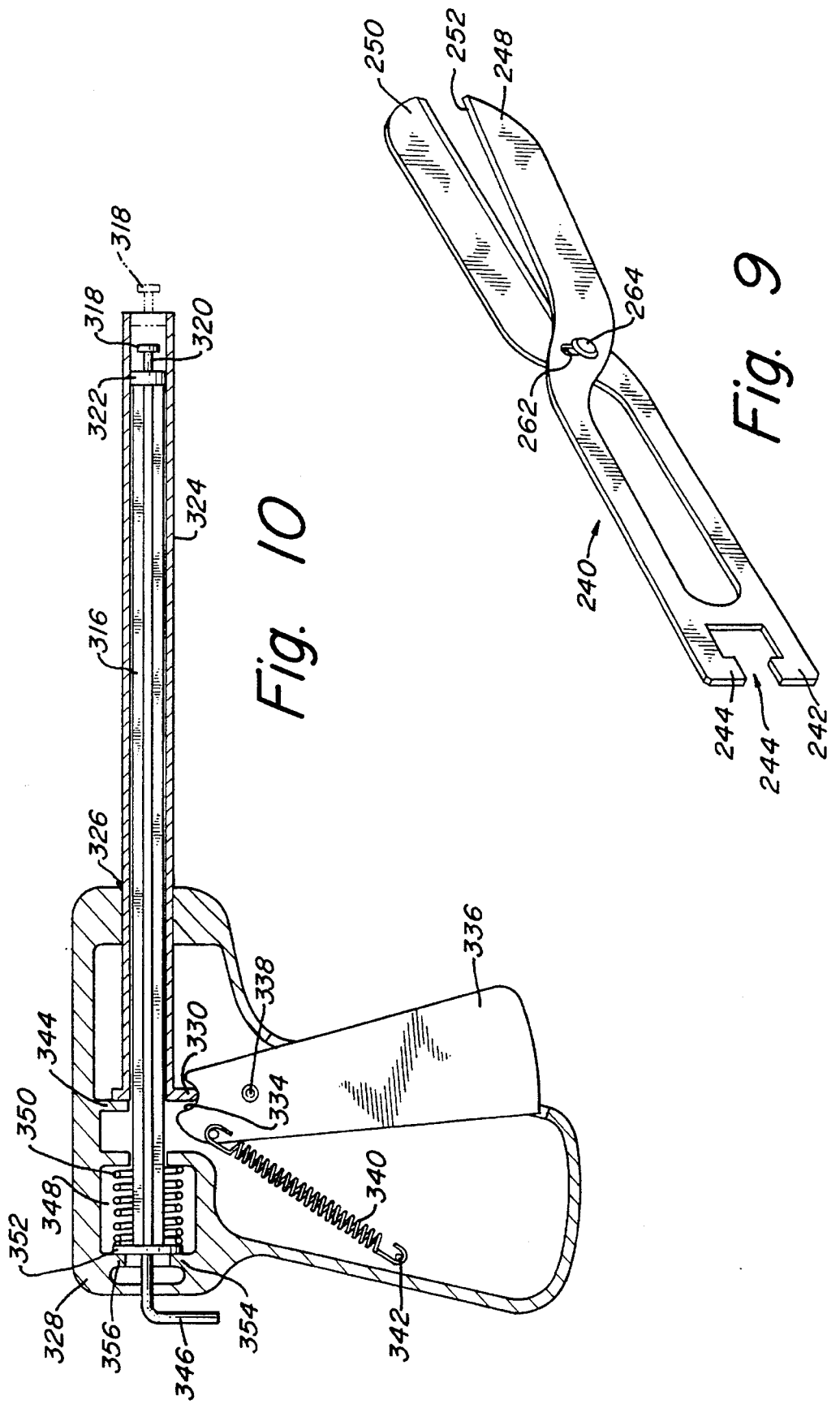

SURGICAL APPARATUS

This is a continuation of application Ser. No. 629,993, filed Dec. 19, 1990, entitled "Surgical Apparatus", now abandoned, which, in turn, is a continuation of application Ser. No. 303,850, filed Jan. 30, 1989, entitled "Surgical Apparatus", now abandoned, each of said applications being assigned to the Assignee of the present application.

TECHNICAL FIELD

The present invention relates in general to medical devices and more particularly relates to an apparatus for use in laparoscopic surgery for clipping, cutting or clamping.

BACKGROUND OF THE INVENTION

A number of surgical apparati including clips, scissors and clamps are known in the art. However, these devices are designed primarily for use during open surgery wherein large incisions are utilized to open the body cavity in order to permit access by the surgeon to the surgical site. These apparatus are not suitable for use with laparoscopic procedures.

In the past few years, laparoscopic surgery has become increasingly important and widespread. Development of the laparoscope and its related surgical techniques have made it possible to conduct surgery that is relatively non-invasive to the body, reducing the risk of infection to the patient and trauma to the body. Laparoscopic surgery has several benefits over open surgery as it reduces the chance of infection from airborne materials and also reduces the chance of adhesions resulting from exposure of the interior of the body, a common occurrence in open surgery. Typically, laparoscopic surgery involves utilization of several small incisions in the body, typically the abdomen. The abdomen is then inflated with a gas, such as carbon dioxide gas. Affixed to the incisions are rubber gaskets to contain the carbon dioxide gas within the body cavity. These gaskets are equipped with one-way valves which permit the insertion of equipment, often microsurgical tools, through the gasket and into the body cavity. Through one such incision, a fiberoptic bundle is typically inserted, allowing the surgeon to view the interior of the body on a television monitor. Through the other incision or incisions are inserted various instruments. During a laparoscopic surgery procedure, the surgeon observes the surgical site on the television monitor and manipulates the instruments by viewing them on the monitor. Because laparoscopic surgery is performed by watching the application of microsurgical instruments to the surgical site within a limited viewing space on a television monitor rather than in open view, instruments which are easy to use, and which provide a minimum of movement when actuated are highly desirable to a surgeon.

SUMMARY OF THE INVENTION

In accordance with the present invention, the disclosed surgical apparatus provides a device for use in laparoscopic surgery for clipping, cutting, or clamping. The present invention provides for a probe of a predetermined length which extends from a frame. In one embodiment of the present invention, one end of the probe is slidably engaged and attached to the frame. To the other end of the probe may be fastened a particular microsurgical instrument, such as a clipper, scissors, or clamp. Slidably disposed over the probe is a probe cover which slidably engages the frame at one end and which is open at the end to which the surgical instrument head may be connected. At least a portion of the probe cover forms a sheath conduit which surrounds the instrument end of the probe. Positioned between the end of the probe to which the instrument head is attached and the frame is a sealing means which provides for the sealing of the annular space between the probe and the interior walls of the probe cover. This sealing means provides for the slidable engagement of the probe cover, forming a conduit and completely encircling the axis of the probe. Provided is a means for manipulating the probe cover such that it slides axially over the probe. The axial movement of the probe cover interacts with the instrument end of the probe to provide the desired action of the instrument such as clipping, cutting, or clamping.

In the preferred embodiment, the apparatus consists of a probe body with the proximal end of the probe body slidably engaged and connected to a frame and extending axially therefrom. On the distal end of the probe body is a coupling flange for receiving and attaching instruments such that the instruments may be axially rotated and positioned. Axially disposed over the probe is a probe sleeve which slidably engages the probe and the frame. The probe sleeve is of a sufficient length such that it will extend and by its movement actuate the instrument attached to the end of the probe. At its proximal end the probe cover engages a trigger handle. The trigger handle movably engages the frame and interacts with the probe to cause longitudinal displacement of the probe sleeve in relation to the probe. Preferably, a spring is provided to hold the probe sleeve in a retracted position until actuated by movement of the trigger handle. Attached to the probe may be any of a number of instruments, such as a clamp, clip, or scissors. The instruments are dimensioned such that they will be received by a coupling flange on the distal end of the probe and positioned in a rotatable fashion, and such that when the probe sleeve slides axially over the probe, such axial movement provides actuation of the desired instrument, such as clipping, clamping or cutting. A seal is disposed between the end of the probe to which the instrument is attached and the frame to provide slidable engagement of the seal with the probe cover and also to seal the interior spaces between the probe body and the interior walls of the probe cover.

In yet another embodiment is a probe body of a predetermined length which is rotatably engaged and extends from a frame. Slidably disposed over the probe is a probe sleeve which slidably engages the frame and which is open at the other end. A seal positioned between each end of the probe provides a slidable sealing arrangement between the probe and the interior walls of the probe cover. A spring is mounted on the frame, such that in the normal position the spring engages the probe sleeve to hold the sleeve in a retracted position when pressure is released from the spring. A trigger handle is provided to slidably position the probe cover in relation to the probe.

A number of alternate embodiments are disclosed herein. The embodiments provide for a probe which does not move during actuation of the functioning apparatus located at the end of the probe. Other embodiments are possible and a more complete understanding of the invention and its advantages will be appreciated from the discussion of the various embodiments.

BRIEF DESCRIPTION OF THE DRAWINGS

Further features and advantages of the invention will become more apparent from the following and from the detailed description as illustrated in the accompanying drawings, in which:

FIG. 4 is a side cross-sectional view of another embodiment of the invention which provides a locking mechanism and utilizes a spring operated trigger handle to actuate the instrument of the apparatus;

FIG. 5 is a partial front cross-sectional view of the locking mechanism;

FIG. 6 is a front cross-sectional view of the apparatus illustrating the probe sleeve with the probe disposed therein;

FIG. 7 is an isometric view of the distal end of the probe, seal, cylindrical body and instrument flange;

FIG. 8 is an isometric view of a clamp instrument body;

FIG. 9 is an isometric view of a scissors instrument body; and

FIG. 10 is a side cross-sectional view of another embodiment of the invention utilizing a spring operated probe handle to effect the changing of instrument heads.

DETAILED DESCRIPTION OF THE INVENTION

Figure 1:
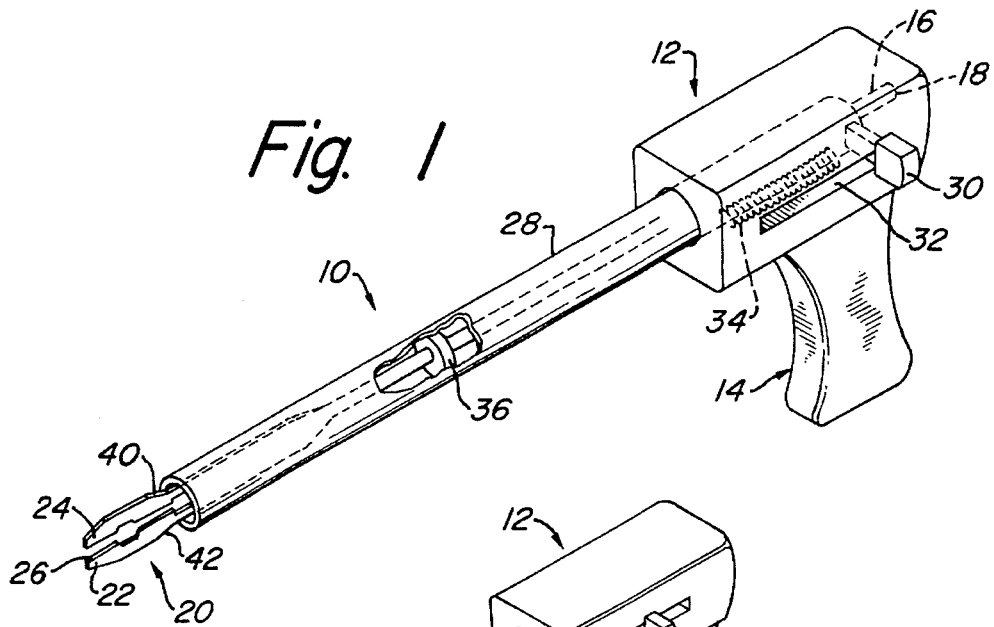
FIG. 1 is an isometric view of one embodiment of the present invention.

FIG. 1 is an isometric view of one embodiment of the present invention. Illustrated is an apparatus for manipulating microsurgical instruments generally indicated as 10. The apparatus 10 has a probe 16 shown partially in phantom, which is attached a one end to a probe frame body 12 at a point of attachment 18 and extending therefrom in an axial direction. Probe frame body 12 has a probe handle grip 14 for grasping the probe frame body 12. At the second end of probe 16 is an instrument head 20 which has two jaws, 22 and 24. When jaws 22 and 24 are positioned in the extended position, the inside surface 26 of jaws 22 and 24 hold a surgical clip. When the jaws are actuated, the clip is compressed to crimp a vein or other tissue. Slidably engaged in the probe frame body 12 is probe sleeve 28. Attached to probe sleeve 28 is actuating arm 30 which extends from the probe frame body 12 through slot 32. Mounted inside the probe frame body 12 is spring 34 which acts in the relaxed position to hold probe sleeve 28 in the rearward position. Preferably, probe sleeve 28 is cylindrical for convenience of manufacture and operation. Disposed between probe sleeve 28 and probe 16 is sealing ring 36 which provides a substantially gas tight seal between the interior wall of probe sleeve 28 and probe 16. This allows for a gas tight seal to be maintained when the apparatus 10 is inserted into the patient. In laparoscopic surgery, the patient's body is normally inflated with an inert gas such as carbon dioxide to permit an unhampered view of the surgical site within the body cavity. Incisions are covered with gaskets having one-way valves to prevent escape of the gas but to allow the insertion of instruments into the body cavity.

Figure 2:
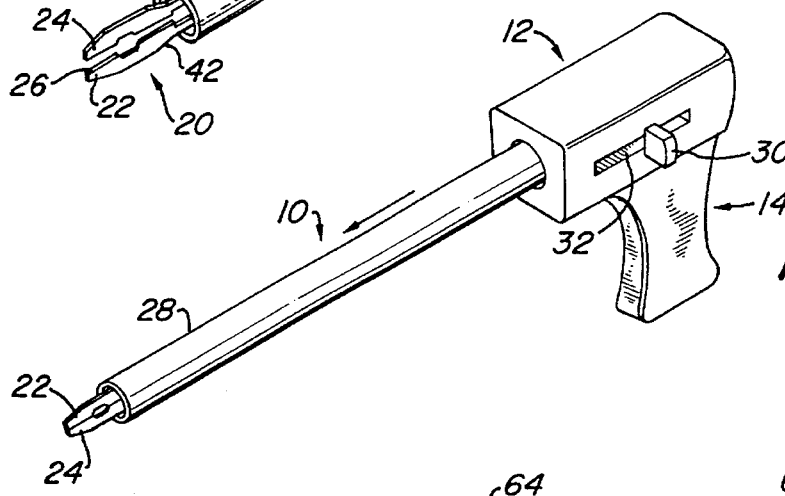
FIG. 2 is an isometric view of the embodiment of FIG. 1 in an actuated position, wherein the probe sleeve compresses the jaws of the instrument head.

In use, a clip is positioned against the inside surface 26 of jaws 22 and 24. The second end of probe 16 which hold instrument head 20 and the distal end of the probe sleeve 28 are inserted through a gasket covering the surgical incision and into the patient. When probe 16 with instrument head 20 and distal end 38 of the probe sleeve 28 enter through the gasket covering the incision, the gasket seals against probe sleeve 28 to prevent the passage of gas between incision and the exterior wall of the probe sleeve 28. Gas is prevented from escaping from the apparatus through the interior of the probe sleeve 28 by sealing ring 36. Once the apparatus is inserted through the gasket covering the incision, the surgeon then positions the surgical clip as held by instrument head 20 in the desired location. Clipping action is accomplished by the forward longitudinal movement of the probe sleeve 28 along the longitudinal axis of probe 16. As shown in FIG. 2, the probe sleeve 28 is moved forward by pushing actuating arm 30 which compresses spring 34 causing probe sleeve 28 to move longitudinally forward and outwardly from the probe frame body 12. As a result of this action, the inner walls of probe sleeve 28 engage camming surfaces 40 and 42 on jaws 22 and 24. As probe sleeve 28 moves forward over jaws 22 and 24, the jaws are pushed together, thereby compressing the clip held in the inside surface 26 between the jaws 22 and 24 as shown in FIG. 2. After the clip is compressed pressure is then released from actuating arm 30 causing spring 32 to relax, forcing the probe sleeve 28 rearwardly into probe frame body 12 and causing jaws 22 and 24 to open. The apparatus 10 may then be removed from the patient incision gasket and another clip may be positioned between jaws 22 and 24, and the procedure repeated the desired number of times. Instrument head 20 as shown in FIG. 1, is a surgical clip applier. Alternatively, the instrument head 20 may be a scissors, clamp or other instrument.

Figure 3:
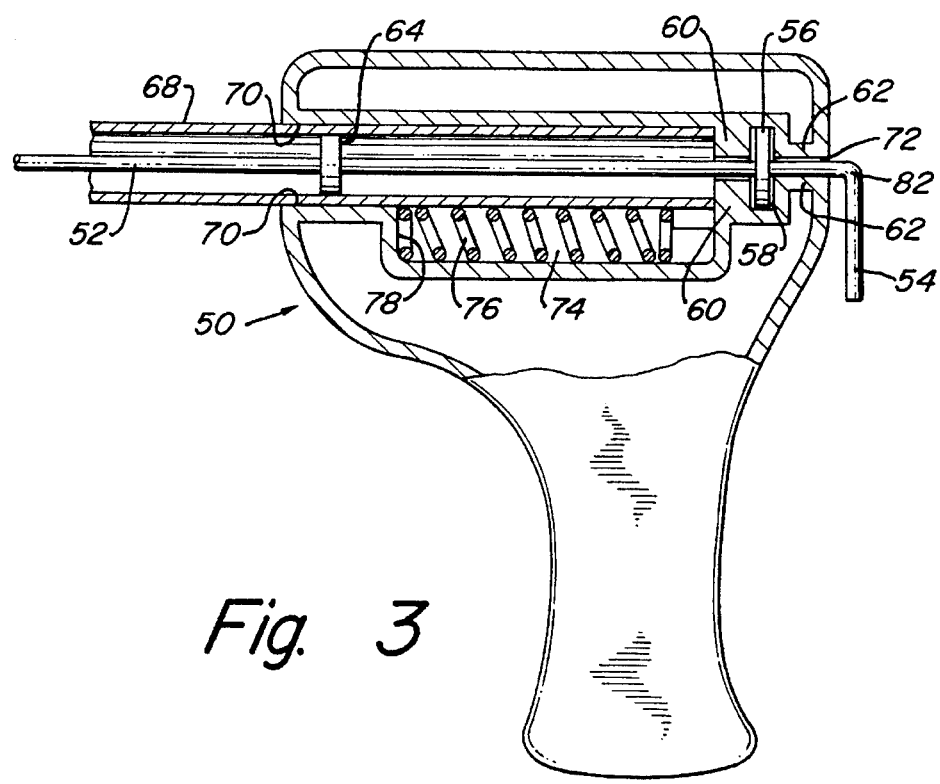
FIG. 3 is a side cross-sectional view of another embodiment of the invention, wherein the probe may be selectively and rotatably positioned.

FIG. 3 illustrates a cross-sectional view of another embodiment of the invention. In FIG. 1, probe 16 is affixed to probe frame body 12 at a point of attachment 18 such that probe 16 is immovable. FIG. 3 shows a cross-sectional view of probe frame body 50 from which probe 52 extends in an axial direction. Probe 52, at the end proximate to the probe frame body has a probe handle 54 for rotating probe 52. Probe 52 is rotatably attached to probe handle 54 by probe flange 56, positioned in flange channel 58 formed by the interior walls 60 and 62 of probe frame body 50. Interior walls 60 and 62 also form a probe passageway 72 in which probe 52 is disposed. Probe flange 56 is rotatably received in flange channel 58 which acts as a bearing to hold probe 52 in alignment. Flange channel 58 holds flange 56 in such a position that longitudinal movement of the probe 52 is prevented. Probe 52 may be provided with one or more sealing flanges 64 which serve as bushings which slidably and rotatably engage the inner walls of probe sleeve 68. The interior walls 60 and 62 of the probe frame body 50 also form a channel 70 which slidably receives probe sleeve 68 to allow movement of probe sleeve 68 along its longitudinal axis and is dimensioned to prevent substantial movement along the latitudinal axis of probe 52. The interior walls 60 and 62 of the probe frame body 50 also form a spring cavity 74 which contains spring 76. The first end of spring 76 engages the interior wall of the probe frame body 50 at the frontal spring cavity face 78 and the second end of the spring 76 engages probe sleeve 68 at the junction of the probe sleeve 68 and actuating arm 82 which extends from the probe frame body 50 through a slot (as illustrated in FIG. 1). Actuating arm 82 acts to engage the forward movement of probe sleeve 68 outwardly from the probe frame body 50 in order to actuate the instrument. In the present invention, instrument head 20 is attached to the distal end of probe 82 and preferably has a slight offset 20A of approximately 10° from the longitudinal axis of probe 52 (as illustrated in FIG. 8). This offset is beneficial in that it improves visibility of instrument head 20 during positioning of the apparatus at the surgical site. The angle of the offset may be varied; however, the angle should not be so great as to impede probe sleeve 68 from slidingly engaging the camming surfaces and actuating the instrument. In the embodiment shown in FIG. 3, probe handle 54 permits positioning of instrument head 20 without the necessity of moving the apparatus as is required with the embodiment shown in FIG. 1.

Another embodiment of the present invention is illustrated in a cross-sectional view in FIG. 4. The apparatus 100 has a probe frame body 102 forming a handle grip 103 for grasping the frame body 102. Attached to probe frame body 102 and extending axially therefrom is probe 104. At the distal end, probe 104 has an instrument flange 106 (FIG. 7) having a cylindrical body 108 adjacent thereto and having a diameter smaller than that of instrument flange 106. Disposed on probe 104, adjacent to cylindrical portion 108 is seal 110 which provides a substantially gas-tight seal between the interior walls of probe sleeve 112 and the probe 104. Attached to the distal end of the probe is instrument head 114. Instrument head 114 has two jaws, 118 and 120, which are positioned in the open or extended position when probe sleeve 112 is in the relaxed, rearward position. Instrument head 114 is rotatably coupled with the distal end of probe 104 by a T-shaped coupling channel 122 which mates with cylindrical body 108 and instrument flange 106 in rotatable engagement. Jaws 118 and 120 of instrument head 114 have camming surfaces 124 and 125 which will slidably engage the inner wall of probe sleeve 112 when it moves forwardly and outwardly from probe frame body 102. This causes the interior wall of distal end 126 of probe sleeve 112 to compress jaws 118 and 120 together to effect the clamping of a vein or artery. Probe sleeve 112 slidably engages and is positioned in passageway 130 formed by the interior walls of probe frame body 102. At the proximal end of probe sleeve 112 is provided probe sleeve flange 132. Located between probe sleeve flange 132 and the distal end of probe sleeve 112 is probe sleeve stop 134, which serves to limit the forward longitudinal movement of probe sleeve 112 to a predetermined distance. A trigger handle 140 is pivotally attached to probe frame body 112 by pin 142 and is provided with notched groove 144 which engages probe sleeve flange 132 of probe sleeve 112. A spring 146 is connected to the interior of trigger handle 140 at point 148 and is connected to probe frame body 102 at point 150. Pressing of trigger handle 140 rearwardly towards probe frame body 102 rotates notched groove 144 forward, engaging probe sleeve flange 132, causing probe sleeve 112 to move in a forward longitudinal direction and over the camming surfaces 124 and 125 of instrument head 114 to actuate the instrument head when the instrument head 114 utilized is a clamp, trigger handle 140 can be provided with a locking groove 160 having a channel 162 that opens to the rear of the trigger handle 140 and opens at the other end into a circular locking slot 164. Trigger handle 140 may be locked in the rearward position by engaging locking pin 170. FIG. 5 illustrates a cross-sectional view of a portion of probe frame body 102 which slidably receives locking pin 170. Locking pin 170 is cylindrical in shape with a first end 172 and a second end 174 of larger diameter and an inner connecting portion 176 of smaller diameter. The two ends 172 and 174 are slidably received by the probe frame body 102. First end 172 is received by one portion of probe frame body 102 and second end 174 is received by the corresponding portion located on the other side of probe frame body 102. FIG. 5 depicts only the portion of probe frame body 102 that engages second end 174 of locking pin 170. First end 172 similarly engages a corresponding portion of probe frame body 102. When locking pin 170 is moved into the second position, shown in phantom, the smaller diameter inner connecting portion 176 aligns with slot channel 162 of locking slot 160. The inner connecting portion 176 is dimensioned with a smaller diameter than that of slot channel 162 such that it will pass through slot channel 162. When trigger handle 140 is held in the fully rearward position, locking pin 170 is positioned such that the first end 172 of locking pin 170 engages the circular locking slot 164 of the handle. Second end 174 of locking pin 170 is dimensioned such that its diameter may not move out of the locked position and forward from the probe frame body until the locking pin 170 is disengaged from the trigger handle 140 by sliding the locking pin 170 to the second position. When the locking slot 160 is engaged, jaws 118 and 120 are held together, permitting the clamping of a blood vessel or other tissue without the need to maintain pressure on trigger handle 140. Once locking pin 170 is disengaged and pressure is released from trigger handle 140, spring 146 returns to its relaxed position, causing trigger handle 140 to pivot to the normal position, causing notched groove 144 to rotate such that probe sleeve 112 is withdrawn rearwardly into the probe frame body 102. Rearward movement of probe sleeve 112 is prevented by counter spring 180 which is mounted at one end to probe frame body 102. Forward movement of counter spring 180 is prevented by spring flange 182 of probe frame body 102. Counter spring 180 partially engages spring flange 182 and partially engages probe sleeve flange 132 of probe sleeve 112. Forward movement of spring 180 is prevented by spring flange 182 and rearward movement of the probe sleeve 112 beyond spring flange 182 is controlled by counter spring 180. Counter spring 180 has sufficient strength to resist further rearward movement of probe sleeve 112 by the force of spring 146. Counter spring 180 may be compressed by the operator grasping probe sleeve 112 and pushing it rearwardly until the distal end 126 of probe sleeve 112 retracts to behind seal 110, thus permitting instrument head 114 to be disengaged from instrument flange 106 and cylindrical body 108 and a different instrument attached to probe 104. Thereafter, the operator releases pressure on probe sleeve 112 and forward movement of counter spring 180 is stopped by spring flange 182. Probe sleeve 112 is then positioned over a portion of the instrument head 114 as shown in FIG. 4, thereby preventing the dislodging of instrument head 114 from the end of probe 104.

FIG. 6 is a cross-sectional view along lines B—B showing probe sleeve 112 and probe 104 disposed therein. Probe 104 is cruciform-shaped with the outer edges 184 slidably engaged with probe sleeve 112, thereby maintaining the orientation of probe sleeve 112 over probe 104.

FIGS. 7, 8 and 9 illustrate the distal end of probe 104 and various instrument heads. Distal end of probe 104 supports a seal 110. Adjacent to seal 110 is a cylindrical body 108 having a first diameter and attached thereto is an instrument flange 106 of a second and larger diameter to which instrument heads may be attached.

FIG. 8 shows a clamp instrument body 200 which may be attached to the distal end of probe 104. At the proximal end, clamp instrument body 200 has a T-shaped channel 210 formed by projections 212. In the preferred embodiment, T-shaped channel 210 is dimensioned such that it rotatably engages cylindrical body 108 and instrument flange 106 projecting from probe 104, such that the top portion of T-shaped channel 210 receives instrument flange 106 and the bottom portion of T-shaped channel 210 receives cylindrical body 108. Preferably, the inner surface 214 of projections 212 are curved to mate with the diameter of cylindrical body 108. Extending from the distal end of clamp instrument body 200 are jaws 118 and 120. In the preferred embodiment, the plane of jaws 216 and 218 is offset from the plane of clamp instrument body 200 by about 10° (FIG. 4). The inner surface 220 of jaws 118 and 120 may be provided with grooves 222 to receive and hold a surgical clip.

FIG. 9 illustrates a scissors instrument body 240 which may be attached to the distal end of probe 104. At the proximal end, scissors instrument body 240 has a T-shaped channel 244 form by projections 246. The dimensions of T-shaped channel 244 are such as to enable scissors instrument body 240 to receive and rotatably engage instrument flange 106 and cylindrical body 108. At the distal end, scissors instrument body 240 has projections 248 and 250 extending therefrom and forming a scissors. Attached to projection 248 and extending perpendicularly therefrom toward projection 250 is pin 262. Projection 250 forms channel slot 264 positioned such that it corresponds in location on projection 250 to the perpendicularly extending pin 262 from projection 248. Pin 262 extending perpendicularly from projection 248 extends through channel slot 264 and slideably engages projections 248 and 250. The diameter of the distal end of pin 262 which extends through channel slot 264 is larger and securely slideably engages projections 248 and 250. The inner edges of projections 248 and 250 are preferably beveled to provide a cutting surface. Pin 262 in communication with channel slot 264 slideably engages projections 248 and 250 to provide a scissors cutting surface 252. Pin 262 in communication with channel slot 264 does not restrict upward and downward motion of the projections. Pin 262 in communication with channel slot 264 simply secures the projections in such a fashion to form a cutting surface 252. Channel slot 264 is larger in diameter than pin 262 and allows the projections 248 and 250 to move toward each other when pressure is applied and to move in opposite directions when pressure is removed.

It will be clear to those skilled in the art that it is not necessary to provide for the rearward movement of probe sleeve 112 for the interchanging of instrument heads. Rather, separate instruments having rotatable instrument heads may be manufactured. Also, the embodiment of FIG. 1 can be provided with an instrument head which is rotatable by providing an instrument flange and cylindrical body of such as those illustrated in FIG. 7. This permits the instrument head to be oriented prior to insertion of the instrument in the incision gasket and into the patient. In the event a different orientation is desired, the apparatus may be removed from the patient and the instrument head rotated to the desired orientation and reinserted into the patient.

FIG. 10 shows another embodiment of the present invention. Again, a probe 316 is provided having one end adapted for receiving an instrument in rotatable attachment, comprising an instrument flange 318 adjacent to a cylindrical body 320 of reduced diameter. A seal 322 is provided to seal the interior walls of probe sleeve 324 which slidably engages seal 322. At its proximal end, probe 316 slidably engages probe sleeve passageway 326 formed by the interior walls of probe frame body 328. A probe sleeve flange 330 is provided on the proximal end of probe sleeve 324 and engages notched groove 334 of trigger handle 336. Trigger handle 336 is pivotally attached to probe frame body 328 by pin 338. Attached to the trigger handle 336 is spring 340, which is anchored to probe frame body 326 at point 342. Pressing trigger handle 336 towards probe frame body 328 causes the notched groove 334 to rotate forward, engaging flange 330 causing probe sleeve 324 to move outward and in the forward direction, actuating an instrument head attached at the distal end of probe 316. Upon release of the pressure on trigger handle 336, spring 340 relaxes, causing notched groove 334 to rotate rearwardly, retracting probe sleeve 324 into the probe sleeve passageway 326 of probe frame body 328 until probe sleeve flange 330 rests on probe sleeve stop 344, preventing further rearward movement of the probe sleeve 324. In the embodiment illustrated in FIG. 10, probe 316 slidably engages probe frame body 328 and has a probe handle 346 protruding from the rear of the probe frame body 328. Probe frame body 328 forms a spring cavity 348 containing probe spring 350. Probe spring 350 has a washer 352 on the proximal end which partially engages a probe flange 354 extending from probe 316. Probe spring 350 forces probe 316 rearwardly until probe 316 rests on probe stop 356 formed by the interior walls of probe frame body 328. In operation during a surgical procedure, probe 316 remains in the rearward position. When removed from the patient, probe handle 346 may be depressed, thereby extending the distal end of probe 316 beyond probe sleeve 324, as shown in phantom. This permits access to the distal end of probe 316 containing instrument flange 318 and cylindrical body 320 such that the instrument head may be changed on the end of probe 316. Once the instrument head is replaced, pressure is released from probe handle 346 and probe 316 returns to the relaxed rearward position such that probe sleeve 324 extends over a portion of the instrument head and the instrument head is rotatably engaged with the end of probe 316.

One skilled in the art will recognize at once that it would be possible to construct the present invention from a variety of materials. Suitable materials include stainless steel and a wide variety of plastics used in the medical field. Preferably the apparatus is constructed of stainless steel and plastic. Generally, the handle is of dimensions suitable to be gripped by the hand and the probe has a length of about 11 inches. Preferably, the probe and probe sleeve are also made from stainless steel. Stainless steel tubing with an outside diameter of about 0.312 inches and an inside diameter of about 0.242 inches has been found suitable. The diameter of the apparatus is a matter of choice; however, it should be below about 0.5 inches in diameter to be compatible with laparoscopic procedures. Other materials may be used which are suitable for use in the surgical field. The probe frame body is preferably made from a plastic such as polycarbonate, polystyrene, or ABS. The body may alternatively be constructed from stainless steel. The seal is generally constructed of a material which will provide for easy sliding, such as Teflon or Delrin (an acetal homopolymer or copolymer).

While the preferred embodiment of the present invention has been described in detail and shown in the accompanying drawings, it will be evident that various further modifications and uses not illustrated are possible without departing from the scope of the invention.

What is claimed is:

1. A surgical instrument for use in applying clips to tissue, the instrument adapted for passage through a surgical sleeve or cannula and into a bodily cavity, the instrument comprising:

a handle for gripping by a user's hand;

an elongate probe extending from the handle and adapted for passage through the surgical sleeve, the probe including:

a generally tubular probe sleeve extending from the handle; and a probe member extending from the handle, generally concentrically through the probe sleeve, and terminating in an end;

a pair of jaws rotatably coupled to the end of the probe member, the jaws for selectively compressing the surgical clip about a portion of tissue in the bodily cavity, the jaws including a pair of camming surfaces and extending a fixed axial distance from the handle, at least the jaws being freely rotatable relative to the handle to permit the handle to be rotated with the jaws in a selected position in the bodily cavity;

seal means disposed in the probe to prevent escape of fluid from the bodily cavity through the surgical instrument; and actuator means coupled to the probe to selectively actuate the jaws by longitudinal movement of the probe sleeve over the camming surfaces of the jaws, wherein the jaws remain at the fixed longitudinal distance from the handle.

2. The surgical instrument according to claim 1 wherein the seal means comprises a resilient seal ring disposed in the probe sleeve and sealingly engaging the probe member.

3. A surgical instrument for use dissecting tissue, the instrument adapted for passage through a surgical sleeve or cannula and into a bodily cavity, the instrument comprising:

a handle for gripping by a user's hand;

an elongate probe extending from the handle and adapted for passage through the surgical sleeve, the probe including:
a generally tubular probe sleeve extending from the handle; and
a probe member extending from the handle, generally concentrically through the probe sleeve, and terminating in an end;

a pair of scissor jaws rotatably coupled to the probe member, the scissor jaws for selectively dissecting tissue in the bodily cavity, the jaws including a pair of camming surfaces and extending a fixed axial distance from the handle, at least the scissor jaws being freely rotatable relative to the handle to permit the handle to be rotated with the scissor jaws in a selected position in the bodily cavity;

seal means disposed in the probe to prevent escape of fluid from the bodily cavity through the surgical instrument; and actuator means coupled to the probe to selectively actuate the scissor jaws by longitudinal movement of the probe sleeve over the camming surfaces of the jaws, wherein the jaws remain at the fixed longitudinal distance from the handle.

4. The surgical instrument according to claim 3 wherein the seal means comprises a resilient seal ring disposed in the probe sleeve and sealingly engaging the probe member.

5. A surgical instrument for use in manipulating tissue, the instrument adapted for passage through a surgical sleeve or cannula and into a bodily cavity, the instrument comprising:

a handle for gripping by a user's hand;

an elongate probe extending from the handle and adapted for passage through the surgical sleeve, the probe including:
a generally tubular probe sleeve extending from the handle and
a probe member coupled to the actuator means and extending from the handle, generally concentrically through the probe sleeve, and terminating in an end;

a pair of jaws rotatably coupled to the probe member, the jaws including a pair of camming surfaces and extending a fixed axial distance from the handle, at least the jaws being freely rotatable relative to the handle to permit the handle to be rotated relative to the jaws with the jaws in a selected position in the bodily cavity;

seal means disposed in the probe to prevent escape of fluid from the bodily cavity through the surgical instrument; and actuator means coupled to the probe to selectively actuate the jaws by longitudinal movement of the probe sleeve over the camming surfaces of the jaws, wherein the jaws remain at the fixed longitudinal distance from the handle.

6. The surgical instrument according to claim 5 wherein the jaws are adapted to compress a surgical clip about a portion of tissue in the bodily cavity.

7. The surgical instrument according to claim 5 wherein the jaws are sharpened scissor jaws adapted to dissect tissue in the bodily cavity.

8. The surgical instrument according to claim 5 wherein the seal means comprises a seal ring disposed in the probe sleeve and sealingly engaging the probe member.

* * * * *